(12) United States Patent
Asada et al.

(10) Patent No.: US 7,638,924 B2
(45) Date of Patent: Dec. 29, 2009

(54) METHOD OF DRIVING ULTRASONIC TRANSDUCER

(75) Inventors: Takaaki Asada, Moriyama (JP); Seiichi Morita, Nagaokakyo (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 617 days.

(21) Appl. No.: 10/595,518

(22) PCT Filed: Mar. 29, 2005

(86) PCT No.: PCT/JP2005/005883

§ 371 (c)(1),
(2), (4) Date: Apr. 25, 2006

(87) PCT Pub. No.: WO2005/095946

PCT Pub. Date: Oct. 13, 2005

(65) Prior Publication Data

US 2007/0108871 A1    May 17, 2007

(30) Foreign Application Priority Data

Mar. 31, 2004    (JP) .............................. 2004-103055

(51) Int. Cl.
*H01L 41/08* (2006.01)
(52) U.S. Cl. .................. 310/317; 310/334; 600/437; 600/459; 367/155; 367/157
(58) Field of Classification Search ............... 310/334, 310/317; 600/437, 459; 367/155, 157
See application file for complete search history.

(56) References Cited

U.S. PATENT DOCUMENTS 7,432,638 B2 * 10/2008 Yamashita et al. .......... 310/334

FOREIGN PATENT DOCUMENTS

| JP | 06-30933 A | 2/1994 |
| JP | 2003-37896 A | 2/2003 |
| JP | 2003-259490 A | 9/2003 |

OTHER PUBLICATIONS

International Search Report issued in the corresponding International Application No. PCT/JP2005/005883, mailed on Aug. 16, 2005.
Official communication issued in the counterpart Chinese Application No. 200580001696.9, mailed on Sep. 7, 2007.

* cited by examiner

*Primary Examiner*—J. SanMartin
(74) *Attorney, Agent, or Firm*—Keating and Bennett, LLP

(57) ABSTRACT

An ultrasonic transducer includes a piezoelectric resonator including a pair of electrodes sandwiching a piezoelectric body and provided with the backing layer in contact with one of the electrodes of the piezoelectric resonator and having the same acoustic characteristic impedance as the piezoelectric body. A method includes the step of driving the ultrasonic transducer so as to satisfy a condition: $2Th \leq Td \leq 6Th$ where Th is a propagation time of an ultrasonic wave in the piezoelectric body sandwiched by the pair of electrodes, and Td is a pulse width of a drive pulse driving the piezoelectric resonator.

14 Claims, 14 Drawing Sheets

SAMPLE BONDED WITH EPOXY RESIN

SAMPLE BONDED WITH GLASS

→ TIME

MEASUREMENT RESULT OF A SAMPLE BONDED WITH
A POLYCARBONATE HAVING A THICKNESS OF 0.5 mm

→ TIME

MEASUREMENT RESULT OF A SAMPLE BONDED WITH A
LIQUID CRYSTAL POLYMER HAVING A THICKNESS OF 0.5 mm

FIG.21

| MATERIAL | DENSITY (kg/m³) | SOUND SPEED (m/s) | CHARACTERISTIC IMPEDANCE ($10^6$ kg/s/m²) |
|---|---|---|---|
| POLYCARBONATE | 1171 | 2330 | 2.73 |
| LIQUID CRYSTAL POLYMER | 1824 | 3470 | 6.33 |
| CERAMIC | 7800 | 3950 | 30.8 |
| WATER | 998 | 1483 | 1.48 |

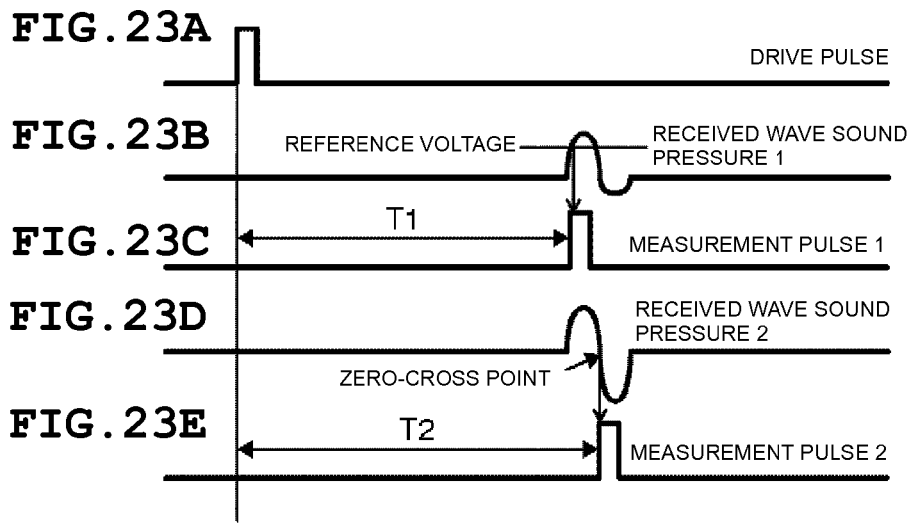
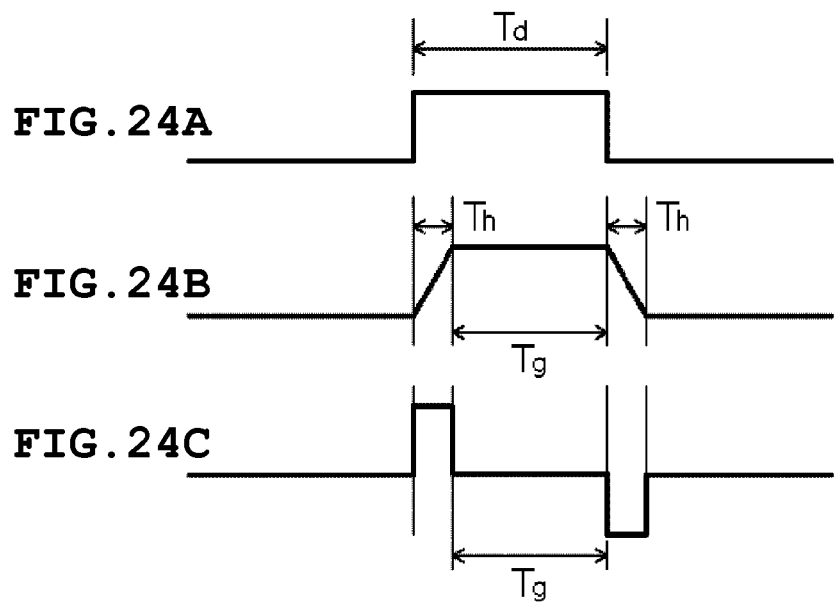
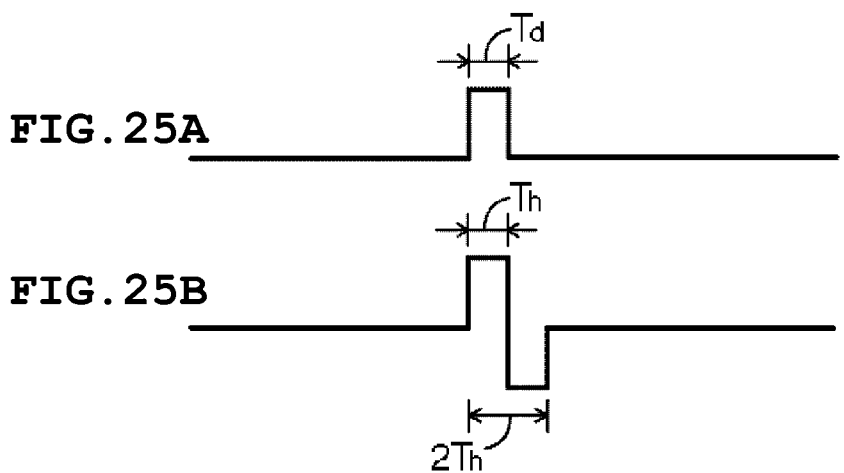

METHOD OF DRIVING ULTRASONIC TRANSDUCER

BACKGROUND OF THE INVENTION

1. Field of the Invention

The present invention relates to a method of driving an ultrasonic transducer for use in measuring sound velocity in a liquid by transmitting and receiving an ultrasonic wave.

2. Description of the Related Art

In general, an ultrasonic transducer has a piezoelectric resonator including a pair of electrodes which sandwich a piezoelectric body, and is provided with a backing layer on the back surface of one of the electrodes of this piezoelectric resonator (for example, see Japanese Unexamined Patent Application Publication No. 2003-259490 (Patent Document 1)). When a drive signal is applied across the pair of electrodes, the piezoelectric resonator is excited to transmit an ultrasonic wave. On the other hand, when an ultrasonic wave is received, the piezoelectric resonator converts the vibration into an electrical signal, and outputs the electrical signal. In addition, the backing layer is provided in order to absorb and attenuate an ultrasonic wave emitted from the piezoelectric resonator to the back surface at the time of excitation.

When sound speeds in various liquids are measured using such an ultrasonic transducer, a pair of ultrasonic transducers are disposed at a predetermined distance from one another, and an ultrasonic wave is transmitted from one of the ultrasonic transducers. The other of the ultrasonic transducers receives the ultrasonic wave that has passed through a liquid. A measurement circuit measures the time required for transmission and receiving, and the sound speed in the liquid is calculated on the basis of the measured time and the distance between both of the ultrasonic transducers.

In this case, when the difference of the acoustic characteristic impedance (acoustic characteristic impedance) of the piezoelectric resonator and that of the backing layer disposed on the back surface thereof is large, the reflection of a sound wave occurs on the boundary surface of both layers to cause resonance in the piezoelectric body, and thus, a phenomenon in which vibration continues without converging in a short time, namely so-called ringing, occurs due to the resonance. When this ringing occurs, a ringing component is included in the signal of the received wave which causes increases in measurement errors and other problems such as lowering the time resolution. Accordingly, a known ultrasonic transducer has been proposed in which a setting is determined such that the acoustic characteristic impedance of the backing layer has substantially the same value as the acoustic characteristic impedance of the piezoelectric body constituting the piezoelectric resonator, and both of them are integrally bonded (for example, see Japanese Unexamined Patent Application Publication No. 2003-37896 (Patent Document 2)).

Incidentally, when applying a drive pulse to an ultrasonic transducer, the shape of the drive pulse is important. When a piezoelectric body is used in an ultrasonic transducer, the applied voltage pulse (=drive pulse) and the displacement have substantially the same waveform, and the sound pressure and the particle speed of the generated ultrasonic wave pulse has substantially the same waveform as the time differentiation of the applied voltage pulse. That is to say, when the drive pulse is a rectangular wave, the differentiation of a rise of a pulse becomes a peak that rises and falls, whereas a fall of a pulse becomes a valley that falls and rises. In short, when a drive pulse having a rectangular shape is applied, a sound wave is generated by the differentiation value of the pulse. Thus, for example, an ultrasonic waveform having two consecutive changes, a peak and a valley, is generated as a waveform of Td=350 nsec in FIG. 5. In this regard, when the element is driven using, for example, a transistor, the drive current is limited, and thus, the voltage across the terminals of the element is a triangular wave rather than a rectangular wave if the electrostatic capacity thereof is large. This causes a lowering of the sound pressure of the generated ultrasonic pulse, and thus, it is desirable to make the drive current as large as possible and to make the electrostatic capacity of the element as small as possible such that the voltage across the terminals is substantially a rectangular wave at implementation time. When the pulse width is wide, the peak and a valley are separated in time.

On the other hand, when the sound speed in various liquids as described above is measured, measurements are made of the time required from applying a drive pulse shown in FIG. 23A to an ultrasonic transducer to the receiving of the wave. At that time, for example, as shown in FIGS. 23B and 23C, if the receiving side measures T1, which is the time period required for the wave to reach the vicinity of the peak of the waveform or the valley, the measurement is likely to be affected by the gain of an amplifier, noises, and other interference, and thus, the measurement precision is likely to be deteriorated.

Accordingly, up to now, as shown in FIGS. 23D and 23E, the detection has been carried out on T2, which is the time of crossing the point of a zero amplitude during a fall from a peak toward the next valley, namely up to a zero-cross point.

In order to detect the zero-cross point of a received signal with high precision as described above, it is desirable that the gradient of the waveform at the zero-cross point is as sharp as possible. However, in a known technique, the waveform of the drive pulse to be applied to an ultrasonic transducer, particularly the pulse width, has not been fully examined. Thus, measurement errors increase. For example, the detection position is unclear when the zero-cross point is detected. Accordingly, problems, such as the decrease of time resolution, have occurred.

Also, when a setting is determined such that the acoustic characteristic impedance of the backing layer has substantially the same value as the acoustic characteristic impedance of the piezoelectric body defining the piezoelectric resonator as disclosed in Patent Document 2, it is possible to suppress the reflection on the boundary surface of both of the layers to a certain extent.

However, even in this case, the reflection of an ultrasonic wave occurs on the end surface of the open side, which is the opposite side of the backing layer to the boundary surface with the piezoelectric resonator, and thus, this reflection component is transmitted to the receiving side to cause measurement errors. Accordingly, it is necessary to prevent the influence of the reflection on the end surface of the open side of the backing layer.

SUMMARY OF THE INVENTION

To overcome the problems described above, preferred embodiments of the present invention provide a method of driving an ultrasonic transducer capable of increasing the detection precision of the zero-cross point and improving the measurement precision of the ultrasonic wave as compared to known ultrasonic transducers without being influenced by the reflection on the end surface of the open side of the backing layer.

According to a preferred embodiment of the present invention, a method of driving an ultrasonic transducer having a piezoelectric resonator including a pair of electrodes sandwiching a piezoelectric body and provided with a backing layer in contact with one of the electrodes of the piezoelectric resonator and having the same acoustic characteristic impedance as the piezoelectric body is provided, the method including the step of driving the piezoelectric resonator so as to satisfy a condition:

$$2Th \leq Td \leq 6Th$$

where Th is a propagation time of an ultrasonic wave in the piezoelectric body sandwiched by the pair of electrodes, and Td is a pulse width of a drive pulse driving the piezoelectric resonator.

In the method according to this preferred embodiment, a setting is preferably determined so as to satisfy a condition:

$$Td < (2L2+L1)/V$$

where L1 is a thickness of the piezoelectric body sandwiched by the pair of electrodes, L2 is a thickness of the backing layer, and V is a sound speed when an ultrasonic wave propagates in the piezoelectric body and the backing layer.

In the method of driving an ultrasonic transducer according to this preferred embodiment, when a pair of the ultrasonic transducers are disposed opposite to each other and sandwiching a substance to define an ultrasonic transmission target, a setting is preferably determined so as to satisfy a condition:

$$(R^2+X^2)^{1/2} - X > (VM \times Td)$$

where X is a distance between both of the opposite ultrasonic transducers, 2R is a length of a short side or a diameter of an ultrasonic wave emission surface, VM is a sound speed of an ultrasonic wave propagating in the substance, and λ is a wavelength of the ultrasonic wave propagating in the substance, represented by λ=(VM×Td).

In the method of driving an ultrasonic transducer according to this preferred embodiment, when there is a partition wall made of a substance different from a substance of an ultrasonic wave emission surface of the piezoelectric resonator and a substance to be a target of ultrasonic transmission therebetween, a setting is preferably determined so as to satisfy a condition:

$$Td < 2Lw/Vw$$

where Lw is a thickness of the partition wall, and Vw is a sound speed when an ultrasonic wave propagates in the partition wall.

In the method of driving an ultrasonic transducer according to this preferred embodiment, a setting is preferably determined such that an acoustic characteristic impedance has a value between an acoustic characteristic impedance of the piezoelectric resonator and an acoustic characteristic impedance of the substance to be a target of ultrasonic transmission.

With the method of driving an ultrasonic transducer according to various preferred embodiments of the present invention, the pulse width of the drive pulse is set to satisfy a desired condition at the transmission side, and thus, the slope of the waveform at the zero-cross point is sharp at the receiving side. Thus, the detection precision of the zero-cross point is increased. Accordingly, the time resolution improves as compared to when an ultrasonic wave is received, and thereby sound speed can be measured with high precision.

The pulse width of the drive pulse or the thickness of the backing layer is set to satisfy a desired condition at the transmission side, and thus, the receiving side is not influenced by the reflection on the end surface of the open side of the backing layer at an ultrasonic-wave transmission time. Accordingly, the measurement precision of the ultrasonic wave is improved.

In addition, the distance X between the pair of ultrasonic transducers is set to satisfy a desired condition, and thus, the ultrasonic wave is received in a near acoustic field. Accordingly, the influence of a diffracted wave is eliminated, and thus, the measurement precision of the ultrasonic wave is improved.

When there is a partition wall made of a substance different from a substance of an ultrasonic wave emission surface of the piezoelectric resonator and a substance to be a target of ultrasonic transmission therebetween, the pulse width of the drive pulse or the thickness of the partition wall is set to satisfy a desired condition, and thus, the receiving side eliminates the influence of the reflection caused on the partition wall. Accordingly, the time resolution improves when an ultrasonic wave is received, and thereby sound speed is measured with high precision.

Furthermore, an acoustic characteristic impedance has a value between an acoustic characteristic impedance of the piezoelectric resonator and an acoustic characteristic impedance of the substance to be a target of ultrasonic transmission, and thus the amount of attenuation by the reflection of the ultrasonic wave on the partition wall is reduced. Accordingly, an ultrasonic wave is efficiently transmitted toward the receiving side.

According to the preferred embodiments of the present invention, the method of driving an ultrasonic transducer has a piezoelectric resonator including a pair of electrodes sandwiching a piezoelectric body and provided with a backing layer in contacting with one of the electrodes of the piezoelectric resonator and having the same acoustic characteristic impedance as the piezoelectric body, the method including the step of driving the piezoelectric resonator so as to satisfy a condition:

$$2Th \leq Td \leq 6Th \qquad (1)$$

where Th is a propagation time of an ultrasonic wave in the piezoelectric body sandwiched by the pair of electrodes, and Td is a pulse width of a drive pulse driving the piezoelectric resonator.

When measuring sound speeds in various liquids, it is preferable to have the gradient of the waveform at the zero-cross point as sharp as possible in order to detect the zero-cross point of the signal of the received wave with high precision. That is to say, when the pulse width Td of the drive pulse is too wide, the gradient of the waveform at the zero-cross point is reduced, and thus, the zero-cross point becomes unclear. Also, when the pulse width Td is extremely narrow, the signal level is reduced, and thus, the S/N ratio is deteriorated. In addition, the degree of change from a peak to a valley is reduced, and thus, the gradient of the waveform at the zero-cross point is reduced, resulting in an unclear zero-cross point. In contrast, when the pulse width Td of the drive pulse is set so as to satisfy the above-described condition (1), the gradient of the waveform at the zero-cross point is sharp. Accordingly, the detection precision of the zero-cross point is increased, and thus, the measurement precision of the ultrasonic wave is improved.

Also, in the method of driving an ultrasonic transducer according to preferred embodiments of the present invention, when using the above-described driving method, a setting is determined so as to satisfy a condition:

$$Td < (2L2+L1)/V \qquad (2)$$

where L1 is a thickness of the piezoelectric body sandwiched by the pair of electrodes, L2 is a thickness of the backing layer, and V is a sound speed when an ultrasonic wave propagates in the piezoelectric body and the backing layer.

If the thickness L2 of the backing layer is set to satisfy the above-described condition (2) in advance, the ultrasonic wave directly generated from the piezoelectric resonator can be separated in time from the ultrasonic wave reflected on the end surface of the open side of the backing layer. Accordingly, the influence of the ultrasonic wave reflected on the end surface of the open side of the backing layer is eliminated, and thus, the measurement precision of the ultrasonic wave is improved. In this regard, the pulse width Td of the drive pulse may be set to satisfy the above-described condition (2) in place of setting the thickness L2 of the backing layer. When an ultrasonic transducer having the same structure as the transmitter is used as a receiver, the receiver should be set to satisfy the condition (2).

Furthermore, in the method of driving an ultrasonic transducer according to preferred embodiments of the present invention, when a pair of ultrasonic transducers are disposed to sandwich a substance to be an ultrasonic transmission target, a setting is determined so as to satisfy a condition:

$$(R^2+X^2)^{1/2}-X > (VM \times Td) \quad (3)$$

where X is a distance between both of the opposite ultrasonic transducers, 2R is a length of a short side or a diameter of an ultrasonic wave emission surface, VM is a sound speed of an ultrasonic wave propagating in the substance, and λ is a wavelength of the ultrasonic wave propagating in the substance, represented by λ=(VM×Td).

That is to say, the ultrasonic wave to be transmitted includes direct waves simultaneously emitted from substantially the entire transmission surface and the diffracted wave having reverse polarity emitted from the edge portion of the transmission surface. However, when the distance X between the pair of the ultrasonic transducers is set to satisfy the above-described condition (3), the ultrasonic wave is received in a near acoustic field, and thus, it is possible to separate and eliminate the influence of the diffracted wave in time. Accordingly, the measurement precision of the ultrasonic wave is improved.

Moreover, when there is a partition wall made of a substance different from a substance of the ultrasonic wave emission surface of the piezoelectric resonator and a substance to be a target of ultrasonic transmission therebetween, a setting is determined so as to satisfy a condition:

$$Td < 2Lw/Vw \quad (4)$$

where Lw is a thickness of the partition wall, and Vw is a sound speed when an ultrasonic wave propagates in the partition wall.

If the thickness Lw of the partition wall is set to satisfy the above-described condition (4), the influence of the reflection caused on the partition wall at the receiving side is eliminated. That is to say, the ultrasonic wave directly generated from the piezoelectric resonator is separated in time from the ultrasonic wave reflected on the end surface of the partition wall. Accordingly, the time resolution improves when an ultrasonic wave is received, and thereby, a sound speed can be measured with high precision. In this regard, the pulse width Td of the drive pulse may be set to satisfy the above-described condition (4) in place of setting the thickness Lw of the partition wall.

Also, a setting is determined such that an acoustic characteristic impedance of the partition wall has a value between an acoustic characteristic impedance of the piezoelectric resonator and an acoustic characteristic impedance of the substance to be a target of ultrasonic transmission. Thus, the amount of attenuation by the reflection of the ultrasonic wave on the partition wall can be reduced. Accordingly, an ultrasonic wave is efficiently transmitted toward the receiving side. As a matter of course, when an ultrasonic transducer having the same structure as the transmitter is used as a receiver, it is preferable to set the thickness Lw of the partition wall and the acoustic characteristic impedance as described above.

Other features, elements, steps, characteristics and advantages of the present invention will become more apparent from the following detailed description of preferred embodiments of the present invention with reference to the attached drawings.

BRIEF DESCRIPTION OF THE DRAWINGS

FIG. 1A is a sectional view, and FIG. 1B is a sectional view taken along line Z-Z of FIG. 1A.

FIG. 21 is an explanatory diagram showing relationships among the density, the sound speed, and the acoustic characteristic impedance of various materials.

FIG. 10 is used. FIG. 22A is a partially cutaway front view showing the state in which the ultrasonic transmitter/receiver is attached, FIG. 22B is a side view thereof, and FIG. 22C is a sectional view taken along line Y-Y of FIG. 22A.

FIGS. 23A-23E are timing charts showing relationships among a drive pulse, received ultrasonic waveforms, and measurement pulses when the sound speed in a substance is measured using the ultrasonic transducer.

FIGS. 24A-24C are waveform charts to be used for an explanation for setting an optimum range of the pulse width of a drive pulse in a method of driving an ultrasonic transducer according to a preferred embodiment of the present invention.

FIGS. 25A and 25B are waveform charts to be used for an explanation for setting an optimum range of the pulse width of a drive pulse in the method of driving the ultrasonic transducer according to a preferred embodiment of the present invention.

DETAILED DESCRIPTION OF PREFERRED EMBODIMENTS

In the following, a description will be given of specific preferred embodiments of the method of driving an ultrasonic transducer.

First Preferred Embodiment

Figure 1A:
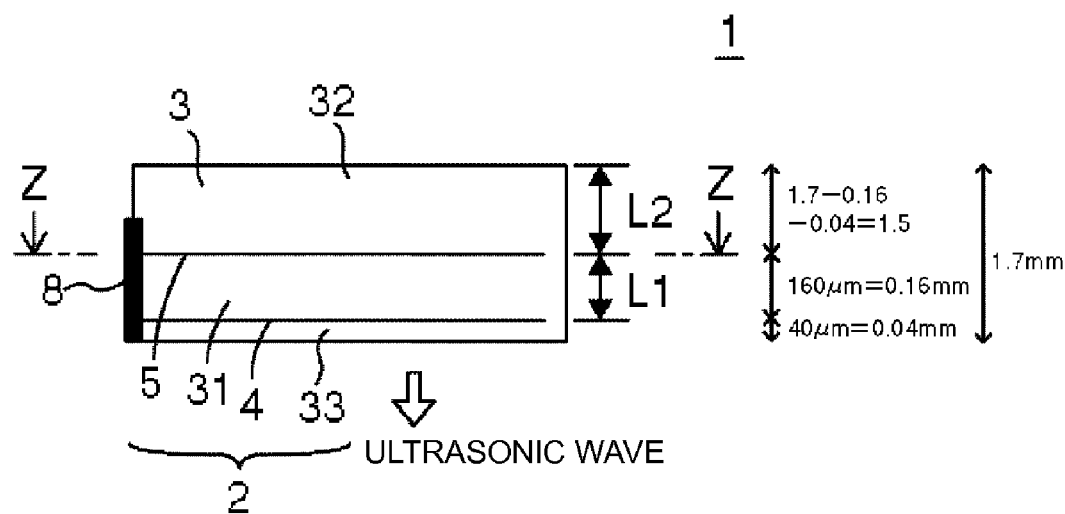
FIGS. 1A and 1B illustrate the configuration of an ultrasonic transducer in a first preferred embodiment of the present invention.
Figure 1B:
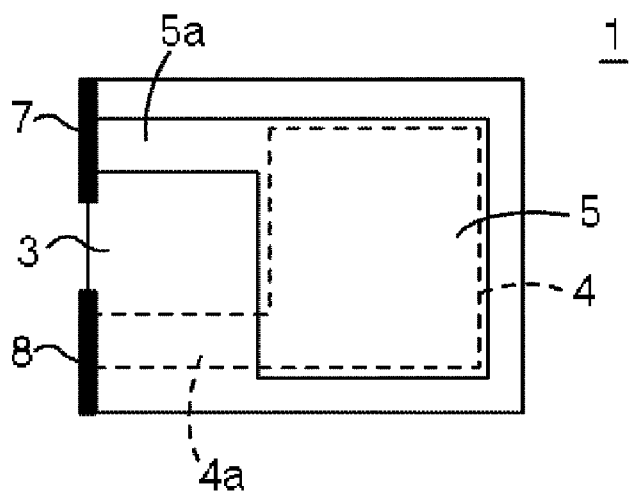
Figure 2A:
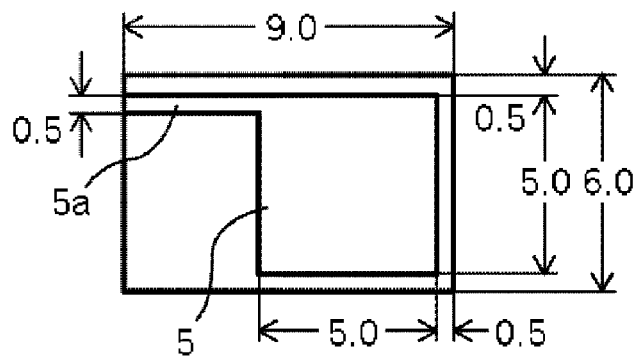
FIGS. 2A and 2B are planar sectional views illustrating the specific size and shape of the electrode of the ultrasonic transducer shown in FIG. 1.
Figure 2B:
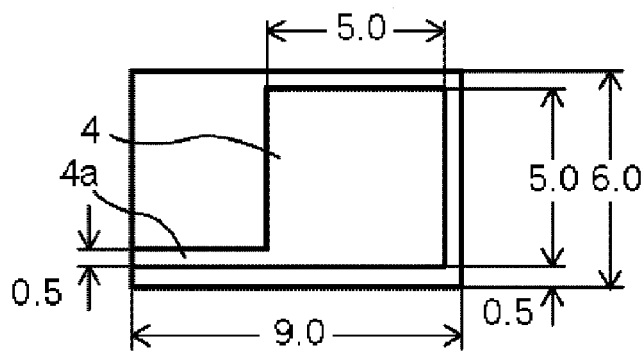

FIGS. 1A and 1B illustrate the configuration of an ultrasonic transducer in a first preferred embodiment of the present invention. FIG. 1A is a sectional view, and FIG. 1B is a sectional view taken along line Z-Z of FIG. 1A. FIGS. 2A and 2B are planar sectional views illustrating the specific size and shape of the electrode of this ultrasonic transducer.

The ultrasonic transducer 1 of this first preferred embodiment includes a piezoelectric body 3 preferably made of a ceramic material, such as a lead zirconate titanate (PZT) or other suitable ceramic material, and a pair of electrodes 4 and 5 are disposed in the piezoelectric body 3 with a predetermined distance therebetween. The portion of the piezoelectric body 3 sandwiched by the pair of electrodes 4 and 5 is subjected to polarization processing to define a piezoelectric active portion 31. Thus, a piezoelectric resonator 2 is defined by this piezoelectric active portion 31 and the pair of electrodes 4 and 5.

Furthermore, the portion of the piezoelectric body located outside of the electrode 5 of the piezoelectric resonator 2 includes a backing layer 32. Also, the outside of the other electrode 4 is provided with a thin outer layer 33. Accordingly, the piezoelectric active portion 31, the backing layer 32, and the outer layer 33, which define the piezoelectric resonator 2, are integrated together to have the same acoustic characteristic impedance. In this regard, the backing layer 32 and the outer layer 33 are non-polarized and in a non-active state, but may have been subjected to polarization processing. Also, external connection electrodes 7 and 8, which are individually connected to the lead-out portions 4a and 5a of the electrodes 4 and 5, respectively, are provided on the end surface of the side that is substantially perpendicular to the electrode-bearing surface of the piezoelectric resonator 2.

In this first preferred embodiment, the ultrasonic transducer 1 having the above-described configuration is produced as follows. First, water and binder are added to a piezoelectric ceramic powder whose main component is a lead zirconate titanate (PZT) to form a sheet. The thickness of one layer of this ceramic sheet is about 65 μm before sintering and about 40 μm after sintering, for example. Silver-palladium paste is printed on the portion corresponding to the electrodes 4 and 5 by a screen printing method. The amount of palladium is preferably in a range of about 0 to about 80% depending on a burning condition and other factors. Here, the amount was determined to be about 30%.

Using the above-described sheets, four layers of the ceramic sheets were laminated to form the piezoelectric active portion 31, 37 layers were laminated to form the backing layer 32, and one layer was laminated to form the outer layer. The sheets were integrally burned at a temperature up to a maximum of about 100° C. The entire dimensions of the ultrasonic transducer 1 were about 6×9×1.7 mm, for example, after burning. At this time, the thickness of the piezoelectric active portion 31 was about 160 μm, the thickness of the backing layer 32 was about 1.5 mm, and the thickness of the outer layer 33 was about 40 μm, for example. Also, as shown in FIG. 2, the thickness of each of the electrodes 4 and 5 is about 1 μm to about 2 μm, the size of the portion of each of the electrodes 4 and 5, which is opposed to the piezoelectric active portion 31, is about 5.5-mm square, and the width of the lead-out portions 4a and 5a is about 0.5 mm. The lead-out portions 4a and 5a are shifted with respect to each other in order not to have piezoelectric activity.

Next, in order to electrically connect each of the electrodes 4 and 5 to the outside, external connection electrodes 6 and 7 were formed on the exposed portion to the side surface of the lead-out portions 4a and 5a of the electrodes 4 and 5. The external connection electrodes 6 and 7 were formed by applying electrode paste made of silver powder and glass powder and burning at a temperature of about 800° C. In this regard, a metal film can be formed by a method using a vacuum technique, such as deposition and sputtering. Next, polarization processing was performed by applying a direct current of about 480 V across both of the external connection electrodes 6 and 7.

Figure 3:
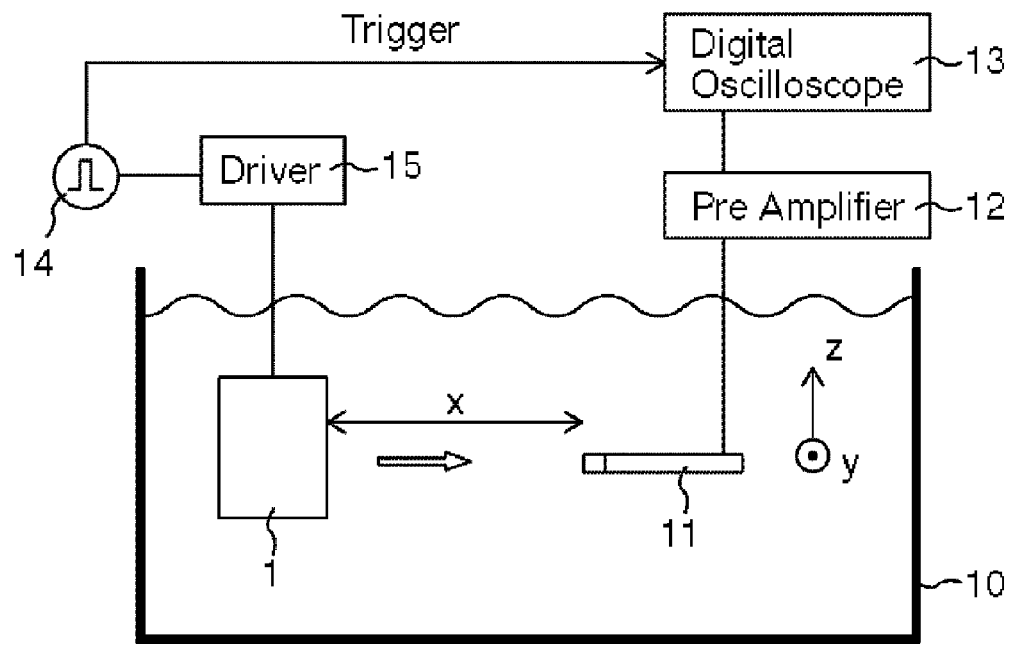
FIG. 3 is a configuration diagram of an apparatus used for observing the received waveform of the ultrasonic wave transmitted from the ultrasonic transducer having the configuration shown in FIGS. 1A and 1B.
Figure 4:
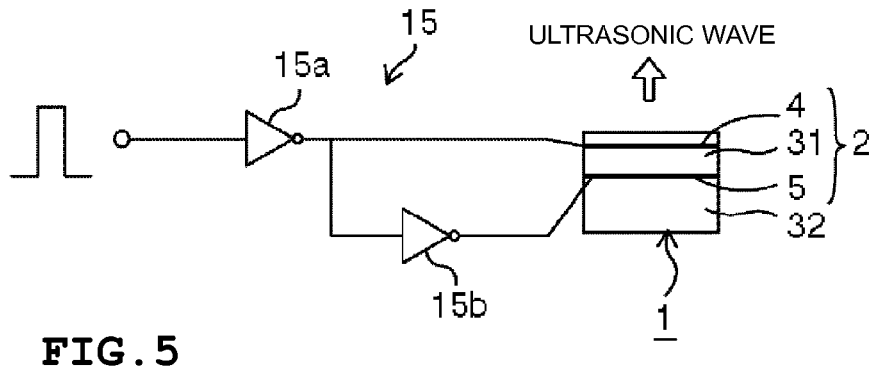
FIG. 4 is an explanatory diagram in the case of applying a drive pulse of the ultrasonic transducer using the same apparatus.

The ultrasonic transducer 1 created in this manner was disposed in a water tank 10 as shown in FIG. 3. The ultrasonic wave emitted from the ultrasonic transducer 1 was received by a PVDF hydrophone 11, and the received waveform was observed by a digital oscilloscope 13 through a pre-amplifier 12. The driving of the ultrasonic transducer 1 was performed by generating a single-shot pulse having various pulse widths by a pulse generator 14 and applying this pulse to the ultrasonic transducer 1 through a driver 15. That is to say, as shown in FIG. 4, a single-shot pulse is directly applied to the electrode 4 through an amplifier 15a using an inverter of the driver 15. Also, the pulse amplified by the amplifier 15a is level-inverted through an inverter 15b, and then is applied to the electrode 5. In this regard, the basic operation is the same in the case of using only one inverter rather than using two inverters. That is to say, in the present invention, the control of the pulse width is important regardless of the driving method.

Figure 5:
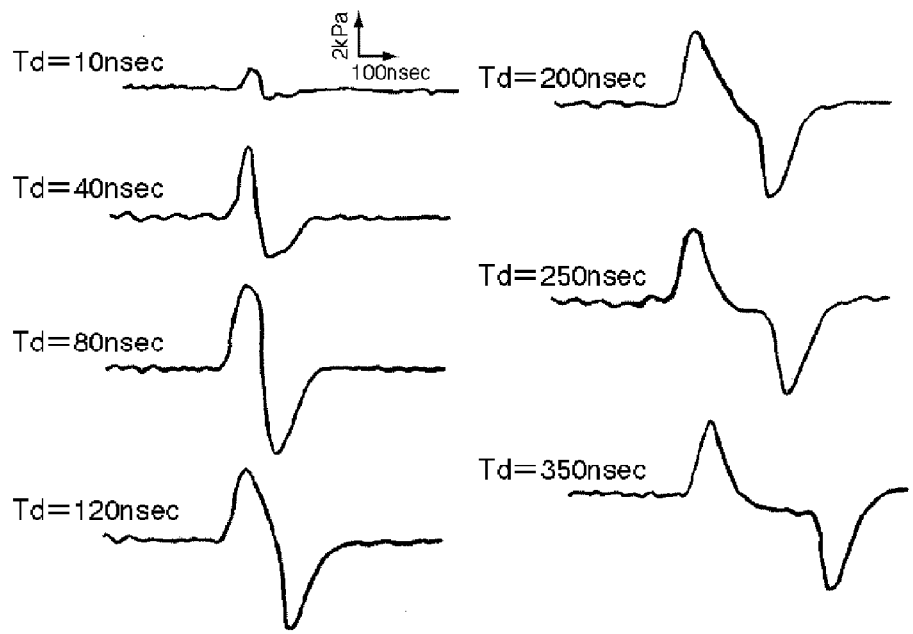
FIG. 5 is a diagram showing the received waveform of the ultrasonic wave obtained when the pulse width of the drive pulse of the ultrasonic transducer is changed using the apparatus shown in FIG. 3.
Figure 6:
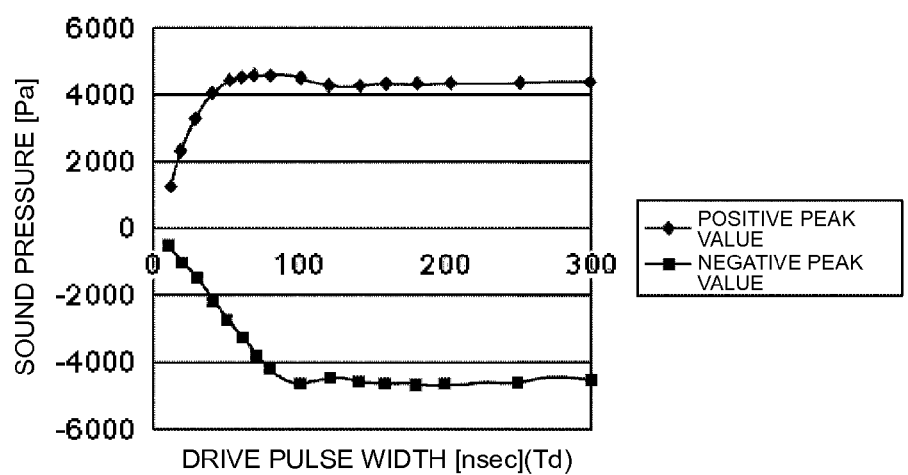
FIG. 6 is a characteristic diagram showing the results of the measurement of each sound pressure of a peak and a valley of the received waveform of the ultrasonic wave obtained when the pulse width of the drive pulse of the ultrasonic transducer is changed using the apparatus shown in FIG. 3.

FIG. 5 shows the waveforms observed at the propagation distance X=5 mm when ultrasonic waves were transmitted by applying a single-shot pulse having various pulse widths Td across both electrodes 4 and 5 of the ultrasonic transducer 1. Also, FIG. 6 shows measured results of individual sound pressures of a peak and a valley of the received waveform when the pulse width Td of the drive pulse is changed.

As understood from these figures, when the pulse width Td is in a small range of less than about 80 nsec, each amplitude of a peak and a valley is also small, the degree of change is mild, the waveforms of a peak and a valley are asymmetric, and thus the zero-cross point is not clear. Also, when the pulse width Td is larger than about 250 nsec, a peak and a valley of the waveform of an ultrasonic wave is separated, the slope of the waveform at the zero-cross point is mild, and thus the detection point at the time of detecting the zero-cross point is unclear.

In contrast, when the pulse width Td is between about 80 nsec and about 250 nsec, the symmetry of a peak and a valley of an ultrasonic waveform is greatly improved, and the gradient of the waveform at the zero-cross point changing from a peak to a valley is relatively sharp. Thus, the zero-cross point can be detected with high precision.

In the first preferred embodiment, the thickness of the piezoelectric active portion 31 defining the piezoelectric resonator 2 is about 160 μm, the sound speed at that time is about 4,000 m/s, and thus, the propagation time Th of the piezoelectric active portion 31 is about 40 nsec. The detection precision of the zero-cross point is greatly improved when the pulse width Td is between about 80 nsec and about 250 nsec as described above. Thus, when specifying the pulse width Td by the propagation time Th, it is understood that the zero-cross point can be detected clearly if the pulse width Td of the drive pulse is set in a range of about two times to about six times the propagation time Th of an ultrasonic wave passing the piezoelectric active portion 32. Accordingly, if the driving is performed by setting the pulse width Td of the drive pulse to satisfy $2 \leq (Td/Th) \leq 6$, namely the above-described condition (1), the zero-cross point can be clearly detected.

Moreover, the optimum range for clearly detecting the zero-cross point is $2 \leq (Td/Th) \leq 3$. The reason for this will be described with reference to FIGS. 24 to 26.

First, an ideal case is considered. When a drive pulse (a pulse width Td) shown in FIG. 24A is applied to the ultrasonic transducer 1, the displacement waveform at that time becomes as shown in FIG. 24B. Also, at this time, the waveform of the sound pressure generated from the ultrasonic transducer 1 becomes as shown in FIG. 24C. In this case, assuming that the displacement waveform requires the time Th at a rise and a fall of the drive pulse, individually, the width of the peak and the width of the valley of the sound waveform become the same Th. In order to have good symmetry in the peak and the valley of the ultrasonic waveform and a sharp slope of the waveform at the zero-cross point, it is required that the time period between the peak and the valley of the ultrasonic waveform $Tg \approx 0$. Accordingly, when Td=Th as shown in FIG. 25A, the optimum ultrasonic waveform is obtained as shown in FIG. 25B.

Figure 26A:
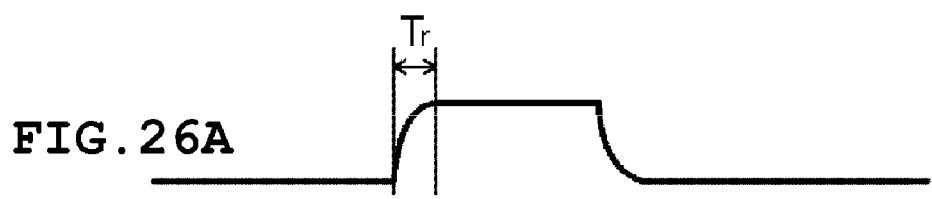
FIGS. 26A-26C are waveform charts to be used for an explanation for setting an optimum range of the pulse width of a drive pulse in the method of driving the ultrasonic transducer according to a preferred embodiment of the present invention.

However, the actual drive pulse has a waveform similar to a waveform of discharging an electrical charge charged in a capacitor through a resistor as shown in FIG. 26A, and thus, the displacement waveform of the ultrasonic transducer 1 requires Tr+Th as the time from the start of the application of the drive pulse to the piezoelectric body 3 to the end as shown in 26B in view of the rise time Tr of the signal. Thus, the waveform of the sound wave generated from the ultrasonic transducer 1 becomes the one as shown in FIG. 26C. Also, in this case, in order to have a sharp slope of the waveform at the zero-cross point, it is required that the time period between the mountain and the valley of the ultrasonic waveform $Tg \approx 0$. Accordingly, the optimum ultrasonic waveform is obtained when $$Td = Tr + Th. \tag{I}$$

Figure 26B:
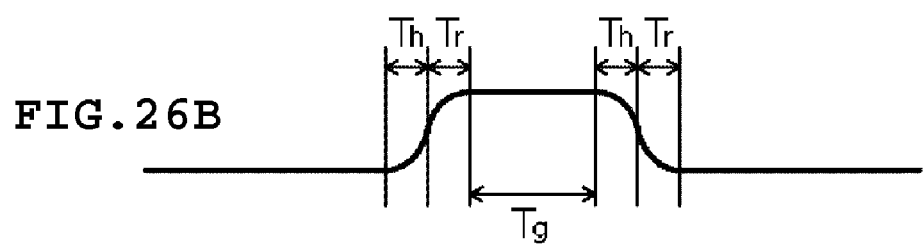
Figure 26C:
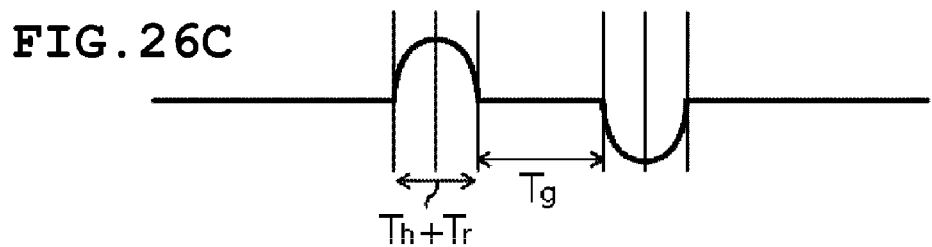

However, the rise time Tr of the signal shown in FIGS. 26A-26C depend on the actual use condition, the circuit configuration, and other factors. The condition for obtaining the maximum voltage by the minimum electric current source is at the time of Th=Tr. When applying this condition to the above-described expression (I), the result becomes Td=2Th, namely Td/Th=2. In reality, Tr becomes somewhat larger than Th, and thus Td/Th=2 shows the lower limit of the optimum range for detecting the zero-cross point clearly.

On the other hand, the upper limit of the optimum range for clearly detecting the zero-cross point depends on the value of Tr. The result of the experiment shown in FIG. 5 indicates that Td/Th=6 (namely, Td=250 nsec) is the upper limit. However, as determined from FIG. 5, when Td/Th=6, the peak and the valley of the ultrasonic waveform are somewhat separated, and thus, the zero-cross point becomes somewhat unclear.

Accordingly, the result of the experiment shown in FIG. 5 indicates that Td/Th=3 (namely, Td=120 nsec) is more desirable.

Second Preferred Embodiment

Figure 7:
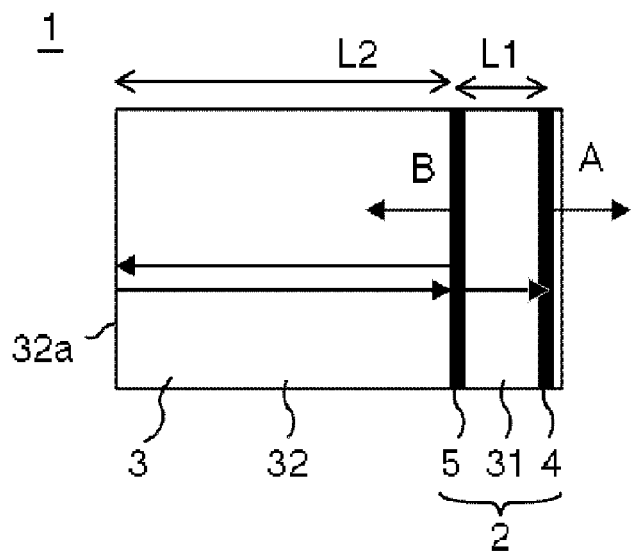
FIG. 7 is an explanatory diagram illustrating a relationship between the ultrasonic wave directly emitted from the emission surface of the piezoelectric resonator and the ultrasonic wave emitted by being reflected from the open end surface of the backing layer and passing through the piezoelectric resonator again in the ultrasonic transducer having the configuration shown in FIGS. 1A and 1B.
Figure 8A:
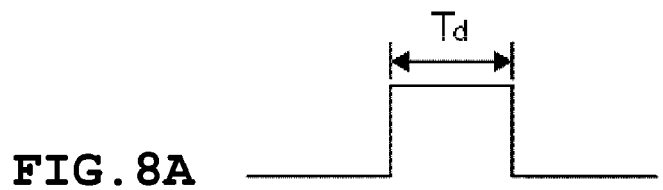
FIGS. 8A and 8B are explanatory diagrams illustrating the comparison between the drive pulse applied to the ultrasonic transducer and the waveform of the received ultrasonic wave.
Figure 8B:
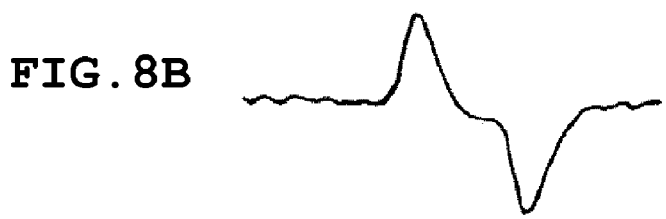

FIG. 7 shows the relationship between the ultrasonic wave directly emitted from the emission surface of the piezoelectric resonator 2 and the ultrasonic wave reflected from the open-end surface 32a of the backing layer 32 and passing through the piezoelectric resonator 2 again to be emitted in the ultrasonic transducer 1 having the configuration shown in FIG. 1. Also, FIGS. 8A and 8B show the comparison between the drive pulse to be added to the ultrasonic transducer 1 and the waveform of the ultrasonic wave at the receiving time.

In the waveform at the time of receiving an ultrasonic wave, the time from the point of a rise of a peak to the zero-cross point is substantially equal to the pulse width Td of the drive pulse. Accordingly, if the time Te, which is required for the ultrasonic wave generated by the piezoelectric resonator 2 to return to the emission surface of the piezoelectric resonator 2 again by being reflected from the open-end surface 32a of the backing layer 32, is greater than the pulse width Td of the drive pulse (Te>Td), the ultrasonic wave directly emitted from the emission surface of the piezoelectric resonator 2 can be separated from the ultrasonic wave reflected from the open-end surface 32a of the backing layer 32 at the receiving side.

Here, assuming that L1 is a thickness of piezoelectric active layer 31, L2 is a thickness of the backing layer 32, and V is a sound speed when an ultrasonic wave propagates in the piezoelectric active layer 31 and the backing layer 32, Te=(2L2+L1)/V. Accordingly, if the thickness L2 of the backing layer 32 is set to satisfy (2L2+L1)/V>Td, that is to say, the above-described condition (2) in advance, the influence of the ultrasonic wave reflected on the end surface of the open side of the backing layer 32 is eliminated. In this regard, the pulse width Td of the drive pulse may be set to satisfy the above-described condition (2) in place of setting the thickness L2 of the backing layer.

Third Preferred Embodiment

Figure 9:
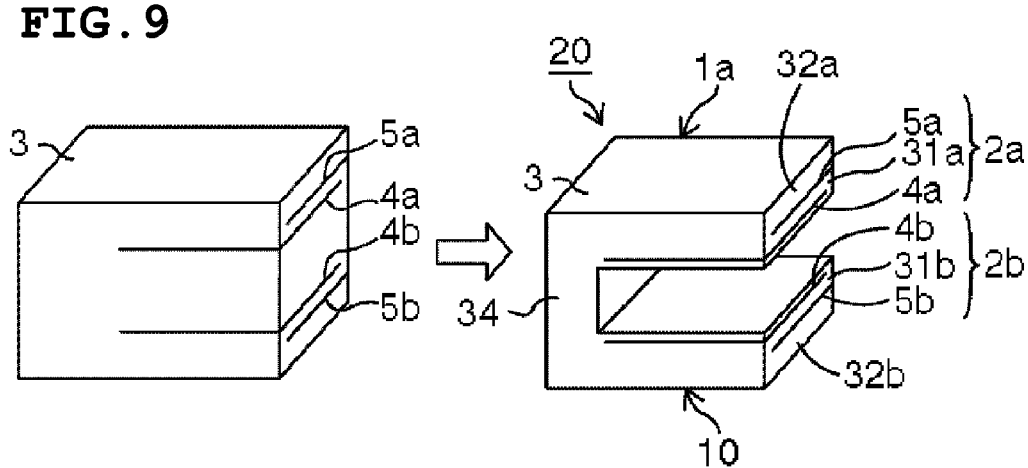
FIG. 9 is an explanatory diagram in the case of configuring an ultrasonic transmitter/receiver by placing opposite a pair of ultrasonic transducers driven with the configuration and the condition described in a first preferred embodiment and a second preferred embodiment of the present invention at a predetermined distance.
Figure 10:
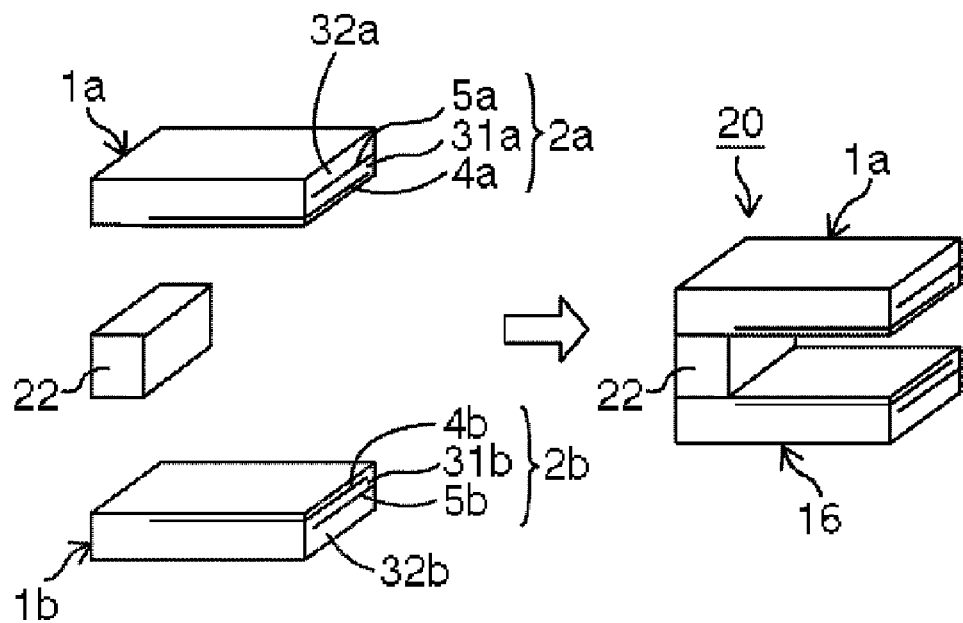
FIG. 10 is an explanatory diagram in the case of configuring another ultrasonic transmitter/receiver by placing opposite a pair of ultrasonic transducers driven with the configuration and the condition described in a first preferred embodiment and a second preferred embodiment of the present invention at a predetermined distance.

FIG. 9 and FIG. 10 are explanatory diagrams when a pair of ultrasonic transducers, which are driven with the configuration and the condition described in the first preferred embodiment and the second preferred embodiment, are disposed opposite at a predetermined distance to define an ultrasonic wave transmitter/receiver.

The ultrasonic wave transmitter/receiver 20 shown in FIG. 9 is produced by forming two pairs of opposed electrodes 4a and 5a, and 4b and 5b in the piezoelectric body 3 and cutting away the central portion located between each pair of the upper and the lower electrodes 4a and 5a, and 4b and 5b into a U-shape by a cutting process. Thus, the ultrasonic wave transmitter/receiver 20 has a configuration in which a pair of ultrasonic transducers 1a and 1b having the same structure as the one shown in FIG. 1 are concatenated through a supporting member 34.

Accordingly, a pair of electrodes 4a and 5a located in the upper portion and the piezoelectric body sandwiched by these electrodes 4a and 5a, that is to say, the piezoelectric active portion 31a defines a piezoelectric resonator 2a, and a backing layer 32a is formed on the back side of one of the electrodes 5a to define one of ultrasonic transducers 2a. Similarly, a pair of electrodes 4b and 5b located in the lower portion and the piezoelectric body sandwiched by these electrodes 4b and 5b, that is to say, the piezoelectric active portion 31b defines a piezoelectric resonator 2b, and a backing layer 32b is formed on the back side of one of the electrodes 5b to define one of the ultrasonic transducers 2b. The ultrasonic wave transmitter/receiver 20 having this configuration has advantages in that it requires only a few production man-hours, and it is easy to align both of the ultrasonic transducers 1a and 1b.

The ultrasonic wave transmitter/receiver 21 shown in FIG. 10 is produced by bonding a pair of ultrasonic transducers 1a and 1b having substantially the same structure as the one shown in FIG. 1, respectively, using a spacer 22 and adhesive in a U-shape.

Here, in the ultrasonic wave transmitters/receivers 20 and 21 shown in FIG. 9 or FIG. 10, the distance X between the ultrasonic wave emission surfaces of a pair of ultrasonic transducers 1a and 1b is preferably set as follows.

Figure 11:
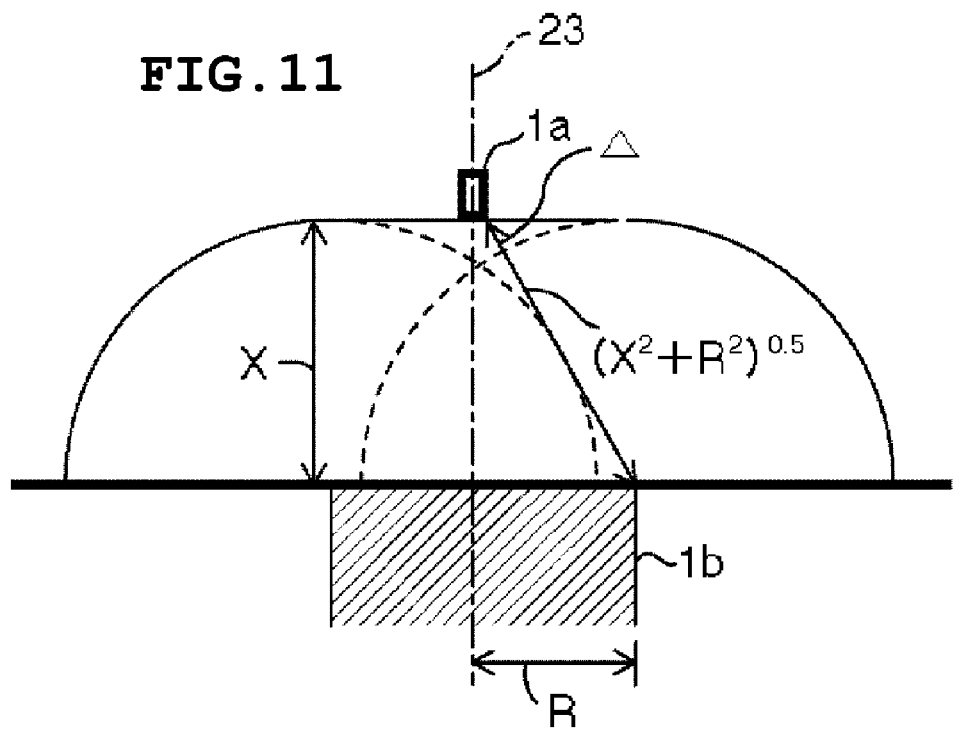
FIG. 11 is an explanatory diagram in the case of setting an opposed distance in order to separate the direct wave and the diffracted wave generated with ultrasonic emission in the ultrasonic transmitter/receiver shown in FIG. 9 or FIG. 10.

As shown in FIG. 11, assuming that an ultrasonic wave is transmitted from one ultrasonic transducer 1b (for example, an upper side) toward the other ultrasonic transducers 1a (here, an upper side), the ultrasonic waves to be transmitted include a direct wave emitted from the transmission surface of the lower-side ultrasonic transducers 1b and a diffracted wave having reverse polarity emitted from the edge portion of the transmission surface.

Figure 12A:
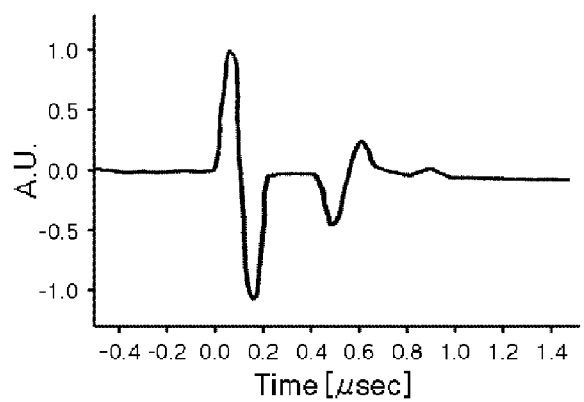
FIGS. 12A and 12B are characteristic diagrams showing the received waveform generated when the opposed distance between a pair of ultrasonic transducers in FIG. 11 is changed.
Figure 12B:
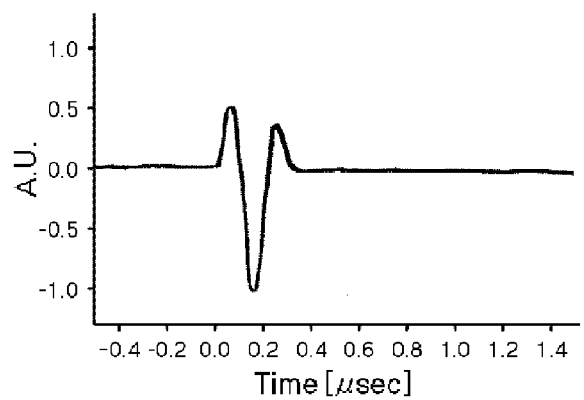

When the direct wave and the diffracted wave arrive at the ultrasonic transducer 1a of the receiving side without overlapping, the zero-cross point from a peak to a valley of the received waveform is clear as shown in FIG. 12A. However, when the direct wave and the diffracted wave arrive at the ultrasonic transducer 1a of the receiving side in an overlapping manner, as shown in FIG. 12B, there are two zero-cross points, from a peak to a valley and from a valley to a peak, of the received waveform before and after in a row, and thus, it is difficult to detect the zero-cross point with high precision. Accordingly, this results in deterioration of the time resolution at the time of receiving an ultrasonic wave.

Here, assuming that X is a distance on an acoustic axis 23 connecting a center of the ultrasonic wave surface of the lower-side ultrasonic transducer 1b and a center of the ultrasonic wave surface of the upper-side ultrasonic transducer 1a, 2R is a length (a diameter when the electrode 4b is a circle) of a short side of the electrode 4b of the ultrasonic-wave emission surface, VM is a sound speed of a ultrasonic wave propagating in the substance sandwiched by the upper and lower ultrasonic transducers 1a and 1b, a wavelength λ of the ultrasonic wave propagating in the substance is represented by λ=VM×Td. A distance from the edge of the ultrasonic wave surface of one of the ultrasonic transducers 1b to the acoustic axis 23 of the ultrasonic wave surface of the other of the ultrasonic transducers 1a is represented by $(R^2+X^2)^{1/2}$.

Now, when an ultrasonic wave emitted from the center of the ultrasonic wave surface of the lower-side ultrasonic transducer 1b travels the distance X and reaches the upper-side ultrasonic transducer 1a, the diffracted wave emitted from the edge also travels the same distance X. In order to separate the direct wave and the diffracted wave in time, it is necessary that the difference of distance $\Delta=(R^2+X^2)^{1/2}-X$ between the direct wave and the diffracted wave at the time of the direct wave reaching the receiving side of the ultrasonic transducer 1a is more than the VM×Td, which is the product of the sound speed VM of a ultrasonic wave propagating in the substance and the pulse width Td of the pulse.

Accordingly, if the opposed distance X is set to satisfy Δ>λ, that is to say, the above-described condition (3), the direct wave and the diffracted wave are separated in time, and the zero-cross point can be detected with high precision. In this regard, it is desirable for the above-described difference of the distance Δ to have a value substantially greater than the wavelength λ. That is to say, it is desirable to be in a near acoustic field. If Δ is too small (that is to say, the opposed distance X is large and in a far acoustic field), the direct wave and the diffracted wave cannot be separated. In this regard, if the ultrasonic transducer of the receiving side is large, the waves are received even when the direct wave and the diffracted wave cannot be separated. However, the direct wave enters with the same phase on the receiving wave surface, whereas the diffracted wave enters with different phases continuously. Thus, the influence of the diffracted wave becomes very small.

Figure 13:
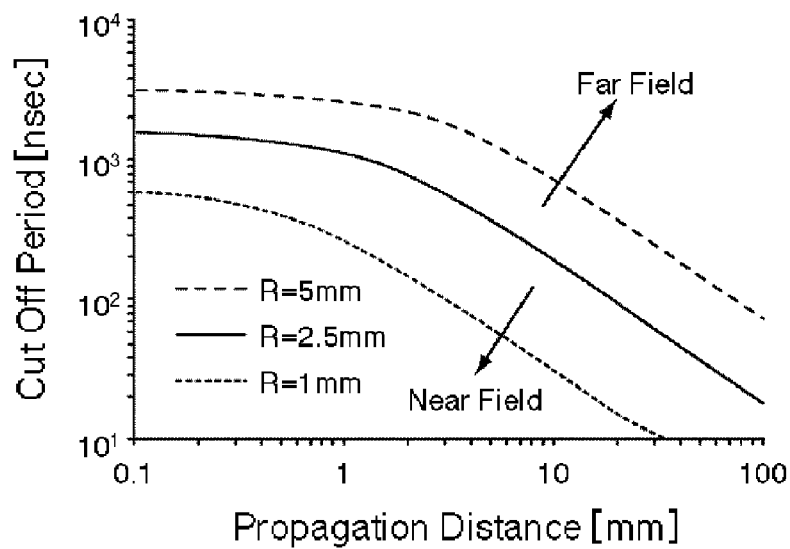
FIG. 13 is a graph plotting $\Delta=\{\sqrt{(R^2+X^2)}\}-X$ using the length of the short side or the diameter 2R of the ultrasonic wave transmission surface as a parameter.

FIG. 13 is a graph plotting $\lambda = \Delta\{\sqrt{(R^2+X^2)}\} - X$ using the length of the short side or the diameter 2R of the ultrasonic wave transmission surface as a parameter. If a point is below this graph, it is in a near acoustic field, and if a point is above, it is in a far acoustic field.

Fourth Preferred Embodiment

In this fourth preferred embodiment, an examination has been made on various characteristics of the ultrasonic wave transmitter/receiver having the configuration of the third preferred embodiment of the present invention shown in FIG. 9 and FIG. 10.

Figure 14:
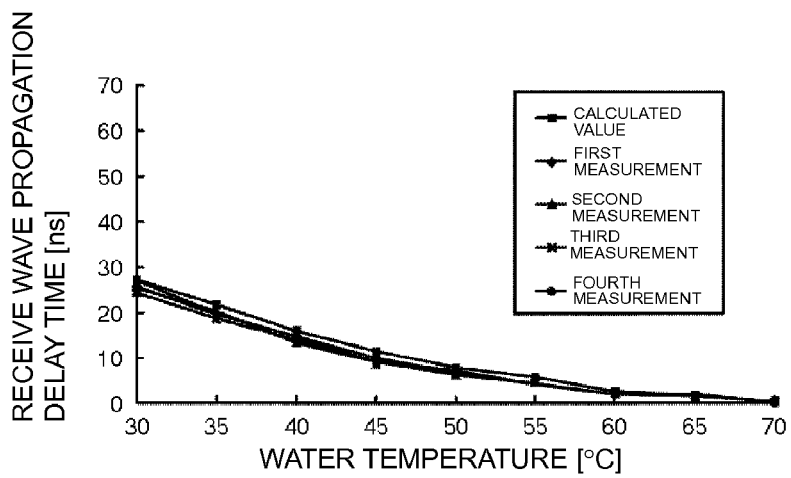
FIG. 14 is a characteristic diagram showing the result obtained by measuring ultrasonic wave propagation time in water, which changes with a water temperature, using the ultrasonic transmitter/receiver having the configuration shown in FIG. 9.

FIG. 14 shows the result obtained by measuring ultrasonic wave propagation time in water, which changes with a water temperature, using the ultrasonic transmitter/receiver 20 having the configuration shown in FIG. 9. In this regard, the value at 70° C. is indicated as 0 nsec here. Also, the calculated value in the same figure was obtained from the distance X≈1.4 mm between the ultrasonic transducers 1a and 1b and the document value. As is understood from FIG. 14, the difference between the measured result and the calculated value is small, and that repeated measurement precision is outstanding.

Figure 15A:
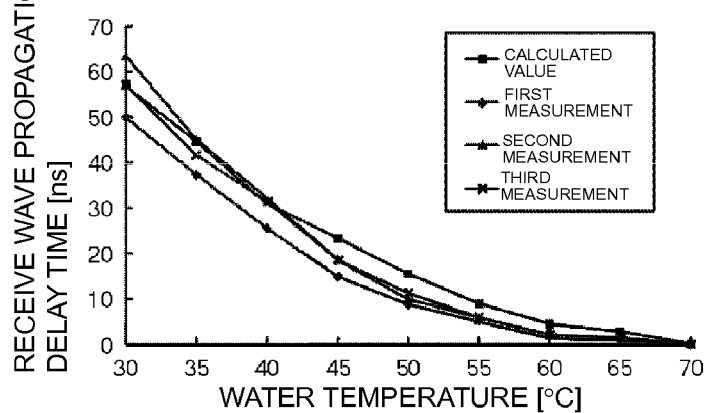
FIGS. 15A and 15B are characteristic diagrams showing the result obtained by measuring ultrasonic wave propagation time in water, which changes with a water temperature, using the ultrasonic transmitter/receiver having the configuration shown in FIG. 10.
Figure 15B:
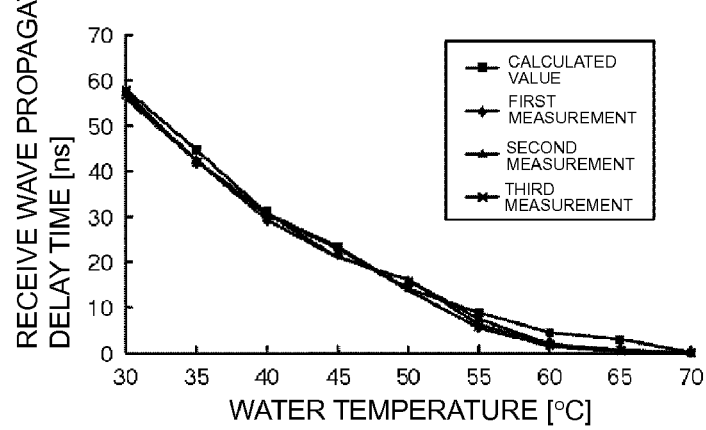

FIGS. 15A and 15B show the results obtained by measuring ultrasonic wave propagation time in water, which changes with the water temperature, using the ultrasonic transmitter/receiver 21 having the configuration shown in FIG. 10. In this regard, FIG. 15A is the case of integrating a pair of ultrasonic transducers 1a and 1b, and the spacer 22 by bonding with epoxy resin. Also, FIG. 15B is the case of integrating a pair of ultrasonic transducers 1a and 1b, and the spacer 22 by bonding with glass.

The comparison FIGS. 15A and 15B shows that the one in which the spacer 22 is bonded with glass has a smaller error from the document value, and a better repetition precision. On the other hand, the one in which the spacer 22 is bonded with epoxy resin has larger variations and a difference from the document values. Thus, it is unsuitable for the case of demanding high time resolution. The reason for this is inferred that the distance between the pair of ultrasonic transducers 1a and 1b has changed by the deformation of the resin due to the change of the water temperature.

Fifth Preferred Embodiment

Figure 16:
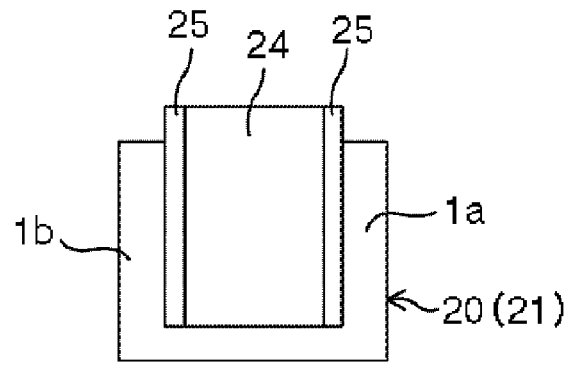
FIG. 16 is an explanatory diagram schematically illustrating the situation in the case where there is a partition wall between a pair of ultrasonic transducers and a substance to be measured.

In this fifth preferred embodiment, in the case of using the ultrasonic transmitters/receivers 20 and 21 having the configuration of the third preferred embodiment shown in FIG. 9 and FIG. 10, for example, as shown in FIG. 16, a partition wall 25, such as a pipe, is disposed between the pair of ultrasonic transducers 1a and 1b, and a substance 24, such as a liquid or other suitable substance, is the target of measurement of the sound speed. The influence to that partition wall 25 is examined. Here, a polycarbonate having a thickness Lw=0.2 mm was used for the partition wall 25, and water was used for the substance 24 through which an ultrasonic wave propagates. The sound speed in the polycarbonate partition wall 25 was about 2,330 m/s.

Figure 17A:
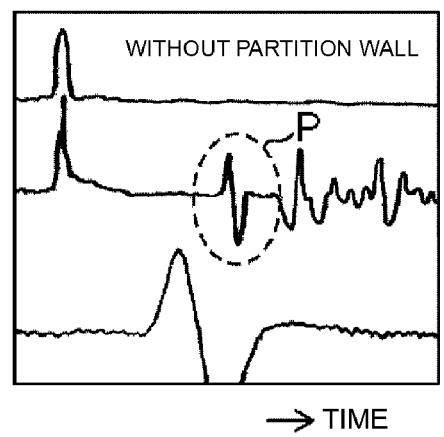
FIGS. 17A and 17B are characteristic diagrams showing a result obtained by measuring the propagation situation of the ultrasonic wave depending on the existence of a partition wall using the ultrasonic transmitter/receiver having the configuration shown in FIG. 9.
Figure 17B:
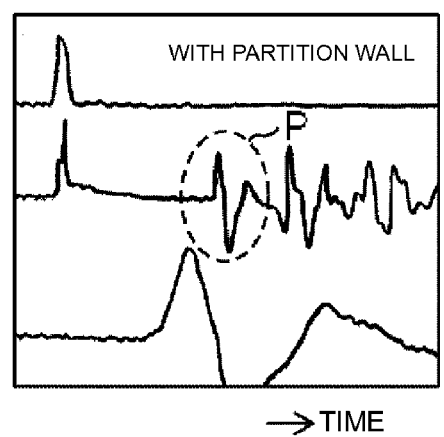

FIG. 17A is a result obtained by measuring the propagation of an ultrasonic wave in a state of dipping in water the ultrasonic transmitter/receiver 20 having the configuration shown in FIG. 9 without change. FIG. 17B is a result obtained by measuring the propagation of an ultrasonic wave in a state of disposing a partition wall 25 between the ultrasonic transmitter/receiver 20 and water 24. In FIGS. 17A and 17B, a curve in the upper row is the waveform of a drive pulse of an amplitude of about 4.5 V and a time width of about 100 nsec. A curve in the middle row is a waveform produced by amplifying the signal propagated to the ultrasonic transducer 1a of the receiving side 20 times. A curve in the lower row is produced by enlarging the portion marked by a reference numeral P of the curve in the middle row. In this regard, adhesive, such as epoxy resin, silicon rubber or other suitable adhesive, are thinly applied to the ultrasonic transmitter/receiver 20 and the partition wall 25.

Figure 18:
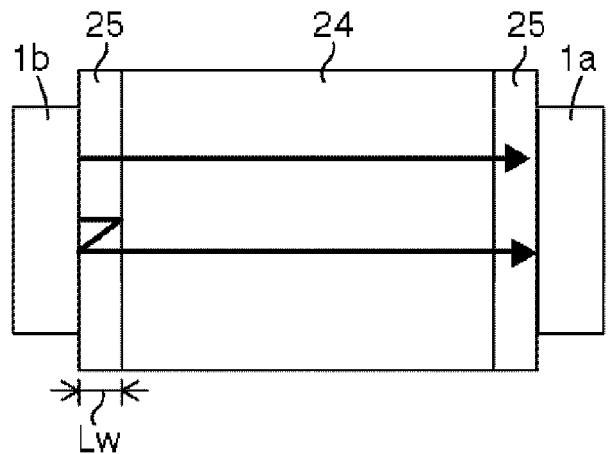
FIG. 18 is an explanatory diagram schematically illustrating the situation in the case where an ultrasonic wave is reflected by the existence of the partition wall when there is a partition wall between a pair of ultrasonic transducers and a substance to be measured.

As is understood from FIGS. 17A and 17B, the transmission and receiving of an ultrasonic wave are possible even if there is a partition wall 25, and significant variations are not produced in the amplitude of the received waveform. However, when there is a partition wall 25 between the ultrasonic transmitter/receiver 20 and water 24, as shown in FIG. 18, ultrasonic waves are received both from the direct wave emitted from the transmission surface of the ultrasonic transducer 1b of the transmission side and the ultrasonic wave reflected on the end surface of the partition wall 25. FIG. 17B shows a state of having received both of such direct wave and the ultrasonic wave reflected on the end surface of the partition wall. Accordingly, when the direct wave and the reflected wave are received in an overlapping state, it is difficult to detect the zero-cross point with high precision.

In order to separate the direct wave emitted from the transmission surface of the ultrasonic transducer 1b of the transmission side and the ultrasonic wave reflected on the end surface of the partition wall 25, the time Tw required for going to and coming back in the partition wall 25 must be greater than the pulse width Td of the drive pulse (Tw>Td). Accordingly, in FIG. 18, assuming that Lw is the thickness of the partition wall 25 and Vw is the sound speed propagated in the partition wall 25, Tw=2Lw/Vw. Thus, if the thickness Lw of the partition wall 25 is set to satisfy 2Lw/Vw>Td, namely the above-described condition (4), the direct wave and the reflected wave are separated in time, and the zero-cross point can be detected with high precision.

Figure 19A:
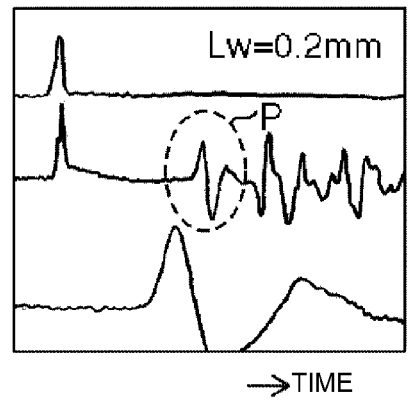
FIGS. 19A and 19B are characteristic diagrams showing the result obtained by measuring the propagation situation of the ultrasonic wave with partition walls having different thicknesses when there is a partition wall between a pair of ultrasonic transducers and a substance to be measured.
Figure 19B:
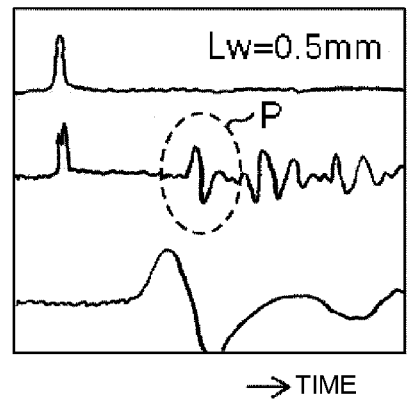

From such a viewpoint, the measurements were made on the propagation of the ultrasonic wave in the case of the partition wall 25 made of a polycarbonate having thicknesses of about 0.2 mm and about 0.5 mm, respectively. The results are shown in FIGS. 19A and 19B. FIG. 19A is the case of the partition wall 25 having the thickness Lw=0.2 mm. FIG. 19B is the case of the partition wall 25 having the thickness Lw=0.5 mm. In each of the figures, a curve in the upper row is the waveform of a drive pulse of an amplitude of about 4.5 V and a time width of about 100 nsec. A curve in the middle row is a waveform produced by amplifying the signal propagated to the ultrasonic transducer 1a of the receiving side 20 times. A curve in the lower row is produced by enlarging the portion marked by a reference numeral P of the curve in the middle row. As shown by the comparison of FIGS. 19A and 19B, if the thickness Lw of the partition wall 25 is set to satisfy the condition of the above-described (4), it is understood that the influence of the reflected wave on the direct wave is eliminated.

Sixth Preferred Embodiment

In this sixth preferred embodiment, as in the above-described fifth preferred embodiment, the influence of the material of the partition wall 25 has been examined when there is a partition wall 25 such as a pipe, between the pair of ultrasonic transducers 1a and 1b, and a substance 24 to be the target of measuring the sound speed.

Figure 20A:
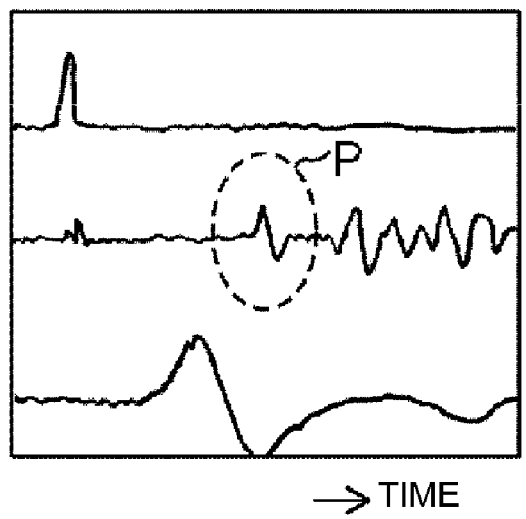
FIGS. 20A and 20B are characteristic diagrams showing the result obtained by measuring the propagation situation of the ultrasonic wave in accordance with the difference of the material of a partition wall using the ultrasonic transmitter/receiver having the configuration shown in FIG. 9.
Figure 20B:
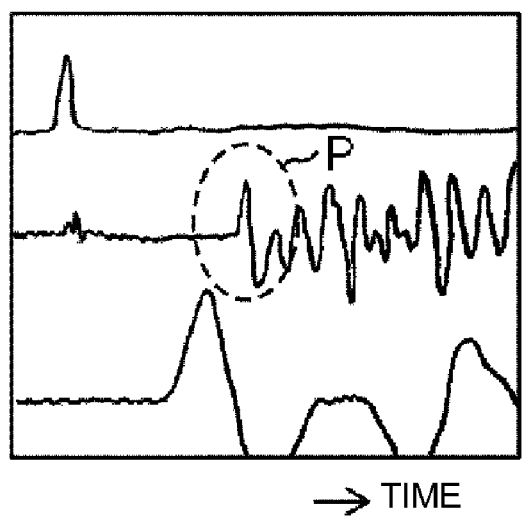

Here, the measurements were made on the propagation state of the ultrasonic waves using a polycarbonate and a liquid crystal polymer as a material of the partition wall 25, individually, the partition wall 25 has a thickness Lw=0.5 mm in both of the cases, and water is used as the substance 24 through which the ultrasonic wave propagates. The results are shown in FIGS. 20A and 20B. FIG. 20A is the case of the partition wall 25 made of a polycarbonate, and FIG. 20B is the case of the partition wall 25 made of a liquid crystal polymer. In each of the figures, a curve in the upper row is the waveform of a drive pulse of an amplitude of about 4.5 V and a time width of about 100 nsec. A curve in the middle row is a waveform produced by amplifying the signal propagated to the ultrasonic transducer 1a of the receiving side 20 times. A curve in the lower row is produced by enlarging the portion marked by a reference numeral P of the curve in the middle row. As is understood from this result, it is possible to transmit and receive ultrasonic waves using not only a polycarbonate but also a liquid crystal polymer as the material of the partition wall 25, and the S/N ratio thereof is outstanding.

As shown in FIG. 21, both of the materials, a polycarbonate and a liquid crystal polymer, defining the partition wall 25 has an acoustic characteristic impedance value between the acoustic characteristic impedance of the piezoelectric ceramic constituting the ultrasonic transducers 1a and 1b and the acoustic characteristic impedance of the substance 24 (here, water) to be the target of the ultrasonic wave transmission. Accordingly, the amount of attenuation by the reflection of the ultrasonic wave on the partition wall 25 is reduced, and thus, an ultrasonic wave is efficiently transmitted to the receiving side.

Figure 22A:
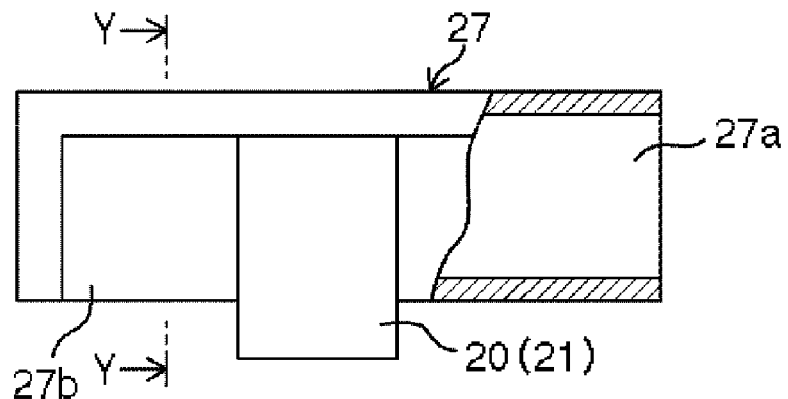
FIGS. 22A-22C illustrate a flow tube to be applied when the ultrasonic transmitter/receiver shown in FIG. 9
Figure 22B:
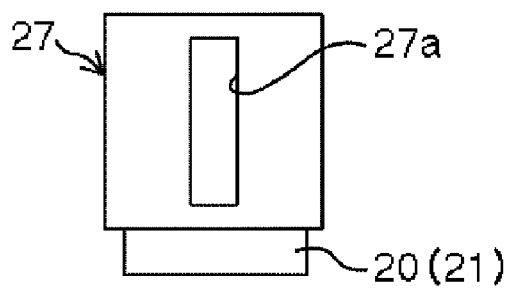
Figure 22C:
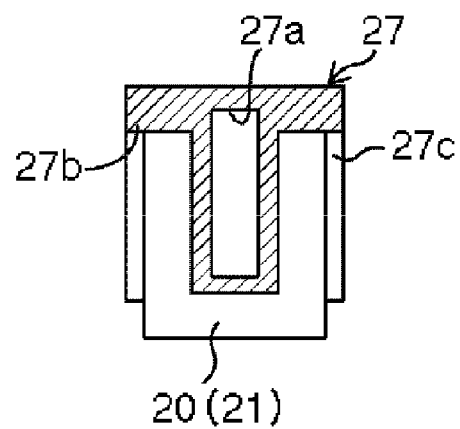

In this regard, when the ultrasonic transmitters/receivers 20 and 21 shown in FIG. 9 or FIG. 10 are actually used, for example a flow tube 27 having a shape as shown in FIGS. 22A-22C can be used. FIG. 22A is a partially cutaway front view showing the state in which the ultrasonic transmitter/receiver is attached, FIG. 22B is a side view thereof, and FIG. 22C is a sectional view taken along line Y-Y of FIG. 22A.

This flow tube 27 is made of a polycarbonate, has a rectangular flow path 27a provided inside in the longitudinal direction, and has concave portions 27b and 27c provided on the right side and the left side, respectively. By attaching each of the ultrasonic transducers 1a and 1b of the ultrasonic transmitters/receivers 20 and 21 shown in FIG. 9 or FIG. 10 in each of the concave portions 27b and 27c, the sound speed of the liquid flowing through the flow path 27a can be measured.

By using such a flow tube 27, when measuring the flow speed of a corrosive liquid flowing through the flow path 27a, the flow speed can be measured without deteriorating the reliability of the ultrasonic transmitters/receivers 20 and 21. Also, for example by attaching an integrated circuit having a function of measuring a temperature, an integrated module of the flow tube 27, the ultrasonic transmitters/receivers 20 and 21, and the integrated circuit is provided. Also, by having such a structure, it is possible to omit the spacer member 22 shown in FIG. 10, and thus, a simpler configuration is provided.

In this regard, in the above-described first to sixth preferred embodiments, piezoelectric ceramic is preferably used for the piezoelectric body 3 of the ultrasonic transducers 1, 1a and 1b. However, the present invention is not limited thereto. For example, it is possible to use a high molecular PVDF piezoelectric body, or other suitable material.

A method of driving an ultrasonic transducer according to preferred embodiments of the present invention can be used for an ultrasonic transducer to measure a sound speed propagating in a medium such as a liquid or other medium.

While preferred embodiments of the present invention have been described above, it is to be understood that variations and modifications will be apparent to those skilled in the art without departing the scope and spirit of the present invention. The scope of the present invention, therefore, is to be determined solely by the following claims.

The invention claimed is:

1. A method of driving an ultrasonic transducer comprising the steps of:
    providing a piezoelectric resonator including a pair of electrodes sandwiching a piezoelectric body, and a backing layer disposed in contact with one of the pair of electrodes of the piezoelectric resonator and having the same acoustic characteristic impedance as the piezoelectric body; and
    driving the ultrasonic transducer so as to satisfy a condition:

$2Th \leq Td \leq 6Th$ where Th is a propagation time of an ultrasonic wave in the piezoelectric body sandwiched by the pair of electrodes, and Td is a pulse width of a drive pulse driving the piezoelectric resonator; wherein
    when a partition wall made of a substance different from a substance of an ultrasonic wave emission surface of the piezoelectric resonator and a substance to be a target of ultrasonic transmission is provided, the method further comprises the step of:
    setting a thickness of the partition wall so as to satisfy a condition:

$Td < 2Lw/Vw$ where Lw is a thickness of the partition wall, and Vw is a sound speed when an ultrasonic wave propagates in the partition wall.

2. A method of driving an ultrasonic transducer comprising the steps of:
    providing a piezoelectric resonator including a pair of electrodes sandwiching a piezoelectric body, and a backing layer disposed in contact with one of the pair of electrodes of the piezoelectric resonator and having the same acoustic characteristic impedance as the piezoelectric body; and
    driving the ultrasonic transducer so as to satisfy a condition:

$2Th \leq Td \leq 6Th$ where Th is a propagation time of an ultrasonic wave in the piezoelectric body sandwiched by the pair of electrodes, and Td is a pulse width of a drive pulse driving the piezoelectric resonator.

3. The method of driving an ultrasonic transducer according to claim 2, further comprising the step of:
    setting a thickness of the piezoelectric body and a thickness of the backing layer so as to satisfy a condition:

$Td < (2L2 + L1)/V$ where L1 is a thickness of the piezoelectric body, L2 is a thickness of the backing layer, and V is a sound speed when an ultrasonic wave propagates in the piezoelectric body and the backing layer.

4. The method of driving an ultrasonic transducer according to claim 2, further comprising the steps of:
providing a pair of the piezoelectric resonators arranged so as to sandwich a substance to be an ultrasonic transmission target; and
configuring the ultrasonic transducer so as to satisfy a condition:

$$(R^2+X^2)^{1/2}-X>(VM\times Td)$$

where X is a distance between the pair of piezoelectric resonators, 2R is a length of a short side or a diameter of an ultrasonic wave emission surface of each of the pair of piezoelectric resonators, VM is a sound speed of an ultrasonic wave propagating in the substance, and $\lambda$ is a wavelength of the ultrasonic wave propagating in the substance, represented by $\lambda=(VM\times Td)$.

5. The method of driving an ultrasonic transducer according to claim 4, wherein the substance is a liquid.

6. The method of driving an ultrasonic transducer according to claim 2, further comprising the steps of:
providing a pair of the piezoelectric resonators;
providing a partition wall made of a substance different from a substance of an ultrasonic wave emission surface of the piezoelectric resonators between the pair of piezoelectric resonators;
providing a substance to be a target of ultrasonic transmission between the pair of piezoelectric resonators; and
setting a thickness of the partition wall so as to satisfy a condition:

$$Td<2Lw/Vw$$

where Lw is a thickness of the partition wall, and Vw is a sound speed when an ultrasonic wave propagates in the partition wall.

7. The method of driving an ultrasonic transducer according to claim 6, wherein the setting step is determined such that an acoustic characteristic impedance of the partition wall has a value between an acoustic characteristic impedance of the piezoelectric resonators and an acoustic characteristic impedance of the substance to be a target of ultrasonic transmission.

8. The method of driving an ultrasonic transducer according to claim 7, wherein the partition wall is attached to the pair of piezoelectric resonators with an adhesive.

9. The method of driving an ultrasonic transducer according to claim 6, wherein the substance is a liquid.

10. The method of driving an ultrasonic transducer according to claim 6, wherein the partition wall is a pipe disposed between the pair of piezoelectric resonators, and the substance is disposed within the pipe.

11. The method of driving an ultrasonic transducer according to claim 6, wherein the partition wall is made of polycarbonate.

12. The method of driving an ultrasonic transducer according to claim 6, wherein the partition wall is made of a liquid crystal polymer.

13. The method of driving an ultrasonic transducer according to claim 2, wherein the step of driving the ultrasonic transducer satisfies a condition:

$$2Th \leq Td \leq 3Th$$

where Th is the propagation time of an ultrasonic wave in the piezoelectric body sandwiched by the pair of electrodes, and Td is the pulse width of a drive pulse driving the piezoelectric resonator.

14. The method of driving an ultrasonic transducer according to claim 2, further comprising the step of providing a thin outer layer disposed in contact with the other of the pair of electrodes of the piezoelectric resonator and having the same acoustic characteristic impedance as the piezoelectric body.

* * * * *

UNITED STATES PATENT AND TRADEMARK OFFICE
CERTIFICATE OF CORRECTION

PATENT NO. : 7,638,924 B2  Page 1 of 1
APPLICATION NO. : 10/595518
DATED : December 29, 2009
INVENTOR(S) : Asada et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 821 days.

Signed and Sealed this

Ninth Day of November, 2010

David J. Kappos
*Director of the United States Patent and Trademark Office*